United States Patent [19]
Fishman

[11] Patent Number: 5,335,670
[45] Date of Patent: * Aug. 9, 1994

[54] ALLERGY TESTING METHOD AND APPARATUS

[76] Inventor: Henry Fishman, 5173 Linnean Ter., NW., Washington, D.C. 20008

[ * ] Notice: The portion of the term of this patent subsequent to Dec. 8, 2004 has been disclaimed.

[21] Appl. No.: 931,202

[22] Filed: Aug. 17, 1992

Related U.S. Application Data

[63] Continuation of Ser. No. 685,626, Apr. 15, 1991, Pat. No. 5,154,181, which is a continuation of Ser. No. 501,376, Mar. 29, 1990, Pat. No. 5,027,826, which is a continuation of Ser. No. 339,863, Apr. 14, 1989, abandoned, which is a continuation of Ser. No. 204,967, May 31, 1988, abandoned, which is a continuation of Ser. No. 88,139, Aug. 21, 1987, abandoned, which is a continuation of Ser. No. 853,710, Apr. 18, 1986, Pat. No. 4,711,247.

[51] Int. Cl.$^5$ .............................................. A61B 10/00
[52] U.S. Cl. .................................... 128/743; 604/47; 604/191; 604/201
[58] Field of Search ................... 128/743; 604/46, 47, 604/181, 191, 201, 244, 411, 413

[56] References Cited

U.S. PATENT DOCUMENTS

| | | | |
|---|---|---|---|
| 2,841,138 | 7/1958 | Laub . | |
| 3,289,670 | 12/1966 | Krug et al. | 604/47 |
| 3,999,543 | 12/1976 | Lacey | 604/413 |
| 4,168,701 | 9/1979 | Chiulli | 604/413 |
| 4,270,548 | 6/1981 | Brennan | 128/743 |
| 4,292,979 | 10/1981 | Ingelfield et al. | 128/743 |
| 4,453,926 | 6/1984 | Galy | 604/47 |
| 4,711,247 | 12/1987 | Fishman | 128/743 |
| 5,027,826 | 7/1991 | Fishman | 128/743 |
| 5,076,282 | 12/1991 | Fishman et al. | 128/743 |
| 5,154,181 | 10/1992 | Fishman | 128/743 |

FOREIGN PATENT DOCUMENTS

| | | | |
|---|---|---|---|
| 913485 | 10/1972 | Canada | 128/743 |
| 325001 | 10/1902 | France . | |

*Primary Examiner*—Randy C. Shay
*Attorney, Agent, or Firm*—Frishauf, Holtz, Goodman & Woodward

[57] ABSTRACT

An allergy testing method and apparatus for testing a patient for a plurality of allergies at substantially the same time, comprises a carrier for receiving a plurality of allergen applying devices, each allergen applying device including a source of an allergen and a movable pricking needle which is movable from an inactive position out of contact with the skin of a patient to an active position for pricking the skin of a patient and applying its associated allergen to the pricked skin when moved from the inactive position to the active position. The carrier holds and supports the plurality of allergen applying devices with a given spacing between each of the pricking needles, and an actuator is coupled to the carrier for moving the pricking needles from their inactive positions to their active positions to prick or pierce the skin of a patient and to thereby apply a respective allergen to the skin of the patient via the pricking needles.

18 Claims, 3 Drawing Sheets

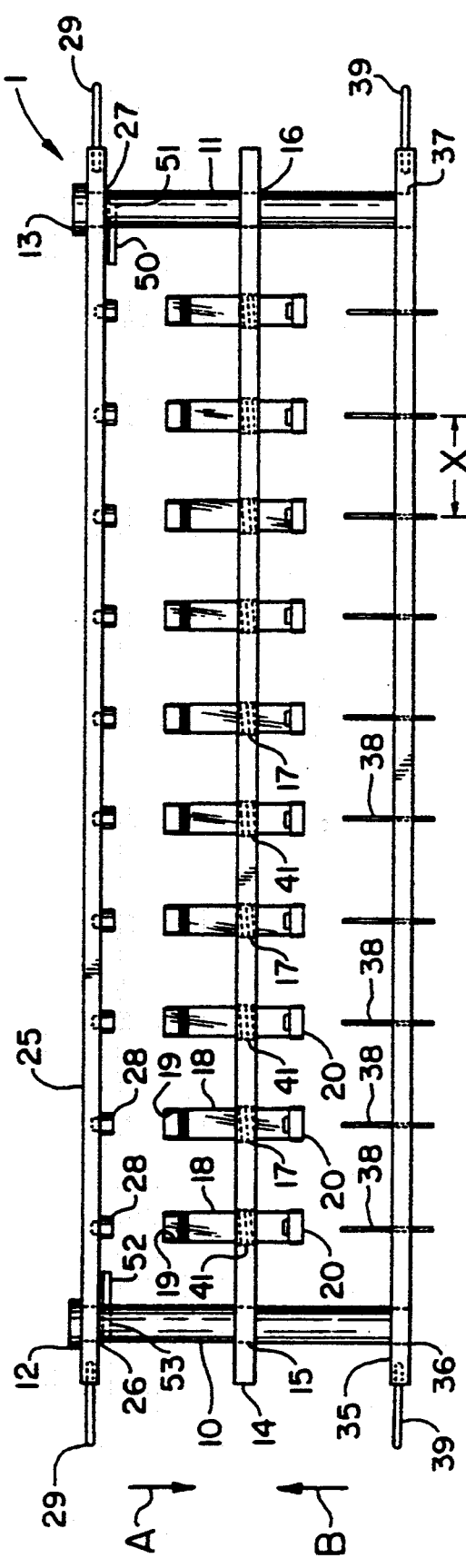
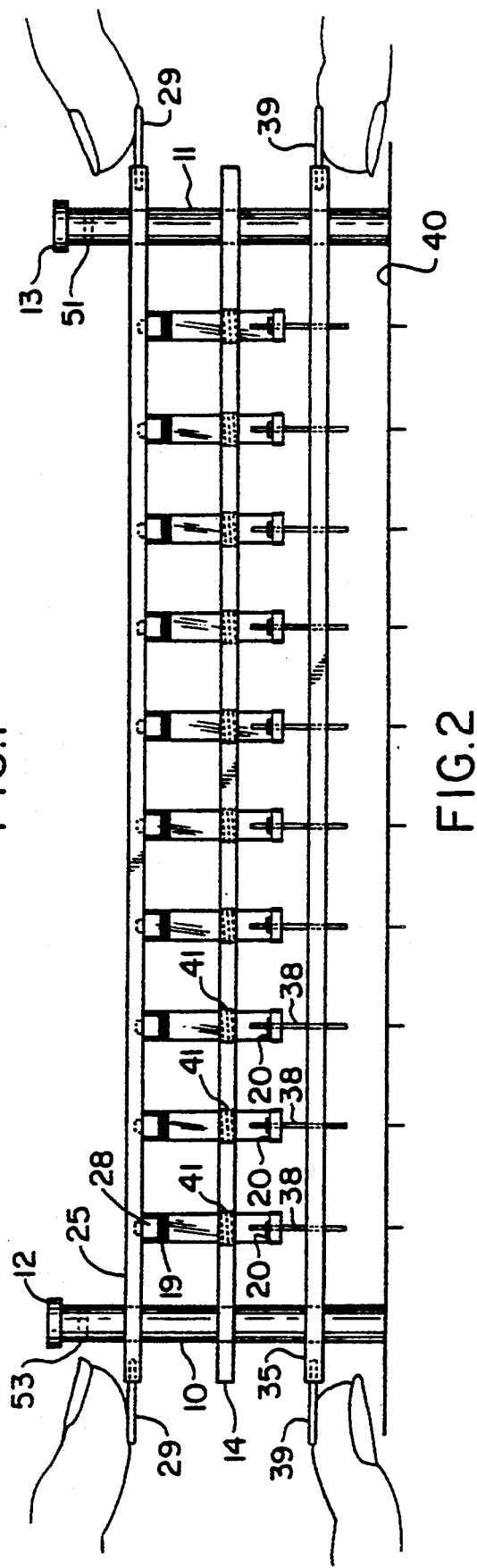

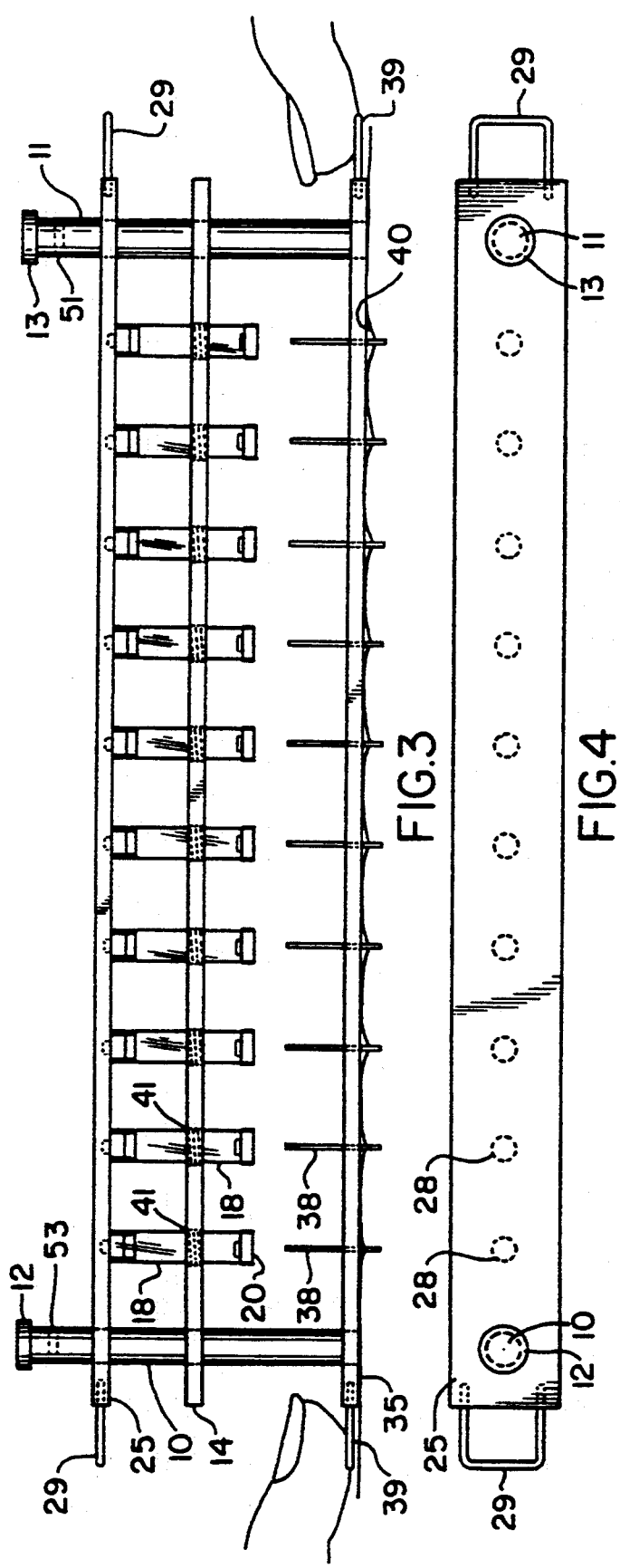
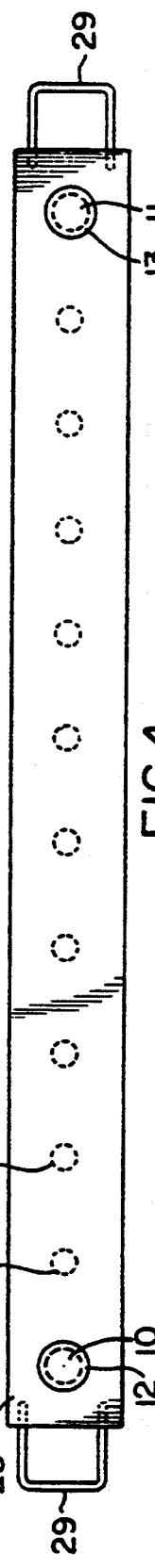
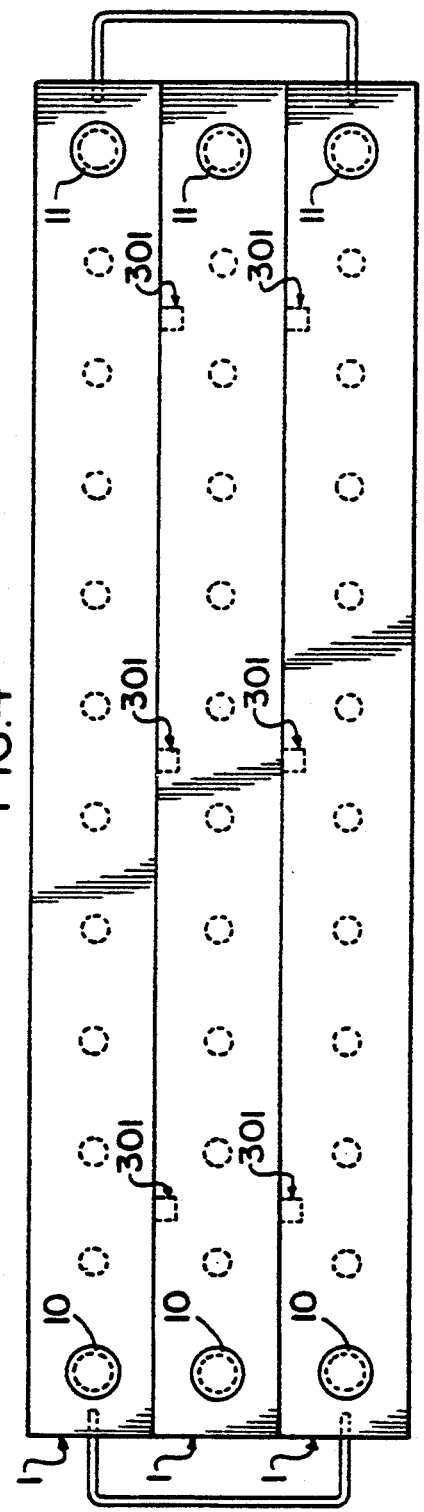
FIG.3
FIG.4
FIG.7

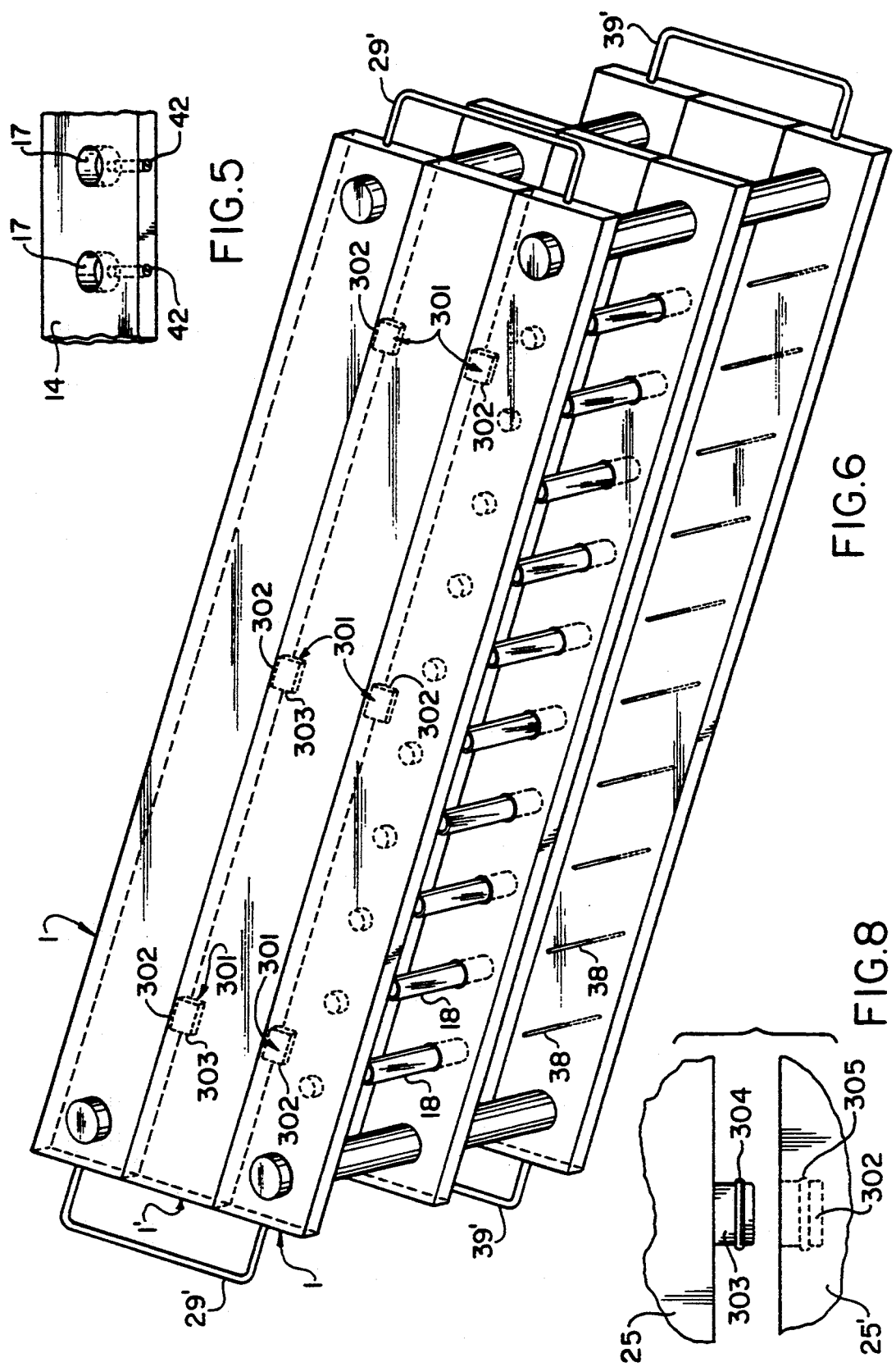

ALLERGY TESTING METHOD AND APPARATUS

This is a continuation, of application Ser. No. 07/685,526 filed Apr. 15, 1991, now U.S. Pat. No. 5,154,181 which is a continuation of application Se No. 07/501,376 file Mar. 29, 1990 (now U.S. Pat. No. 5,027,826), which in turn is a continuation of application Ser. No. 339,863 filed Apr. 14, 1989 (abandoned), which in turn is a continuation application of Ser. No. 07/204,967, filed May 31, 1988 (abandoned), which in turn is a continuation of application Ser. No. 07/088,139 filed Aug. 21, 1987 (abandoned), which in turn is a continuation of application Ser. No. 06/853,710 filed Apr. 18, 1986 (now U.S. Pat. No. 4,711,247).

BACKGROUND OF THE INVENTION

This invention relates to allergy testing methods and apparatuses, and more: specifically to improved apparatuses end methods for testing a patient for a plurality of allergies at substantially the same time.

Allergy testing generally involves giving a patient a plurality of "prick tests." Each prick test is applied in order to determine whether or not a patient is allergic to a particular substance, such as pollen, animal dander, dust, foods, etc. A conventional prick test involves placing a drop of a test substance on the patient's skin and then using a needle to scratch the substance through the skin. If a reaction occurs, the patient is considered to be allergic to the particular substance. At present, allergy testing is carried out on an individual basis. Each test substance is dropped, one drop at a time, on the patient's arm or back. Each drop is then individually pricked through the skin with a separate needle. This is a very time consuming process (for both the patient and the practitioner) and very often involves multiple office visits for the patient. This leads also to a substantial amount of patient discomfort, expense, and inconvenience.

An object of the present invention is to provide improved apparatuses and methods for testing patients for allergic reactions to a plurality of substances, all at substantially the same time. The invention will reduce the time required for testing, minimizing patient discomfort, expense and inconvenience, and improving productivity.

A further object of the invention is to provide improved methods and apparatuses which will enable the plurality of allergy tests to be applied simultaneously without requiring great deal of technical skill on the part of the operator.

Yet another object of the invention is to provide improved apparatuses which used pre-packaged allergen and needles, which are easily insertible in and removable from a carrier, thereby facilitating loading the carrier with predetermined allergens, and improving the sterility of the apparatus.

Still another object is to provide an allergy testing system where the pricking of the skin is always done to a given skin penetration depth which is predictable and which is replicable without requiring highly skilled operators.

SUMMARY OF THE INVENTION

According to an aspect of the invention, an allergy testing apparatus for testing a patient for a plurality of allergies at substantially the same time, comprises carrier means for receiving a plurality of allergen applying means, each allergen applying means including a source of an allergen and a movable pricking means movable from an inactive position out of contact with the skin of a patient to an active position for pricking the skin of a patient and applying its associated allergen to the pricked skin when moved from the inactive position to the active position; said carrier means holding and supporting the plurality of allergen applying means with a given spacing between each of the pricking means; and actuating means coupled to said carrier means for moving the pricking means of each of the allergen applying means from the inactive position to the active position thereof to prick or pierce the skin of a patient and to thereby apply an allergen from a respective allergen applying means to the skin of the patient via the pricking means.

According to another aspect of the invention, an allergy testing method for testing a patient for a plurality of allergies at substantially the same time, comprises providing a plurality of allergen applying means, each including a source of an allergen and movable pricking means for pricking the skin of a patient when moved from an inactive position to an active position; mounting and supporting the plurality of allergen applying means in a support means with a given spacing between each of the pricking means; placing the support means adjacent the skin of a patient; and moving the pricking means of each of the allergen applying means from the inactive position to the active position thereof to prick or pierce the skin of a patient and to thereby apply an allergen from a respective allergen applying means to the skin of the patient via the pricking means.

BRIEF DESCRIPTION OF THE DRAWINGS

FIG. 1 is a side view, in a partially disassembled state, of an embodiment of the present invention;

FIG. 2 is a side view of the embodiment of FIG. 1 arranged ready for use;

FIG. 3 is a side view showing the apparatus of FIGS. 1 and 2 after the needles have pierced or pricked the skin of the patient FIG. 4 is a top view of the embodiment of FIGS. 1-3;

FIG. 5 is a partial view of a modified intermediate plate member;

FIG. 6 is a perspective view of a modified embodiment, including three units of FIGS. 1-4;

FIG. 7 is a top plan view of the embodiment of FIG. 6; and

FIG. 8 is a fractional view of a modified interconnection for use in the embodiment of FIGS. 6 and 7.

DETAILED DESCRIPTION

Referring to FIGS. 1, 2 and 3, an allergy testing unit 1 of the present invention comprises a pair of vertical support posts 10, 11 at opposite ends thereof, the support posts 10, 11 having respective stops 12, 13 at the upper ends thereof. The posts 10, 11 may be made, for example, of plastic material and the end stops 12, 13 can be integrally moulded with the posts 10, 11 respectively. An intermediate plate member 14 has apertures 15, 16 formed at the ends thereof through which the posts 10, 11 respectively pass. The plate number 14 is fixedly connected to and supported by posts 10, 11, for example by an adhesive or the like, in the position shown in FIG. 1. Plate member 14 also comprises a plurality of apertures 17, through which are mounted capsules or vials 18 containing allergens. The capsules 18 have rubber stoppers 19 at the top portions thereof and puncturable rubber seals 20 at the lower portions thereof.

The apparatus further comprises an upper plate member 25 which has apertures 26, 27 therein so as to be slidably mountable on posts 10, 11. If the stops 12, 13 are integrally formed on posts 10, 11, the upper plate is mounted on posts 10, 11 from the bottom, before the intermediate plate 14 is fixed to the posts 10, 11. The upper plate member 25 comprises engaging projecting members 28 which respectively engage into recesses in the upper rubber stopper members 19 of the respective capsules 18, as shown in FIGS. 2 and 3. Upper plate member 25 also comprises handle members 29 at the opposite ends thereof to facilitate handling and griping of the apparatus in use.

The apparatus further comprises a lower plate member 35 having apertures 36, 37 by means of which the lower plate member 35 is slidably mounted on posts 10, 11. Lower plate member 35 has a plurality of hollow needles 38 fixedly mounted therein, the needles 38 preferably having sharp tips at both opposite ends thereof. The needles 38 are mounted in registration with the capsules 18 and projecting members 28. Lower plate member 35 further comprises handles 39 projecting from the opposite ends thereof, similar to the handles 29 of the upper plate member 25 and in registration With handles 29 of upper plate member 25.

As seen in FIG. 1, removable pins 50,52 may be inserted in holes 51,53, respectively, in posts 10,11 to "lock" the upper plate member 25 in its uppermost position. When ready for use, the pins 50,52 may be merely removed by the operator by pulling them out of their respective holes in the posts. Similar pins and holes can be provided in posts 10,11 above The lower plate member 35 in order to physically prevent the lower plate member 35 from moving upwardly, to inadvertently pierce the punctuable rubber seals 20. When ready for use, the pins can, of course, be removed. Other types of locking arrangements could be used in place of pins 50,52 and respective holes 51,53.

FIG. 1 shows the apparatus in its partially assembled state. In operation, the upper plate member 25 is pressed downwardly in the direction of arrow A in FIG. 1, and the lower plate member 35 is pressed upwardly in the direction of the arrow B in FIG. 1 by means of pressing with the fingers of the operator, as shown in FIG. 2, until the apparatus reaches the condition shown in FIG. 2. When the apparatus is in the condition shown in FIG. 2, the posts 10, 11 are placed against the skin 40 of the patient to support the apparatus against the patient's skin, as shown in FIG. 2. In the FIG. 2 condition, the needles 38 are pierced through the respective puncturable seals 20 at the lower portions of the respective capsules 18 and extend into the respective capsules and in contact with the allergens contained with the respective capsules 18. Then, the operator presses the lower plate member 35 downwardly toward the skin 40 as shown in FIG. 3. While pressing downwardly, the needles 38 leave the respective capsules 18 and prick the skin of the patient at predetermined spaced intervals corresponding to the positions at which the needles 38 are fixedly mounted in the lower plate member 35. The allergens which passed into the respective hollow needles 38 are now applied to the pierced or pricked portions of the patient by capillary action. At this point, the upper portion of the unit 1, comprising the posts 10, 11, the upper plate member 25 and the intermediate member 14, can be removed by the operator. The lower plate member 35 can be removed with the other elements of the device or it can remain against the skin of the user for the desired amount of time to permit penetration of the allegen through the needles 38 and into the skin of the patient. After use, the lower plate member 35 along with its needles 38 can either be discarded or sterilized for re-use.

Preferably, the pucturable seals 20 at the lower portions of the respective capsules 18 are of the type that sealingly reclose upon removal: of the needle 38 therefrom. Such seals are well known. Thus, the capsules 18 containing the allergens can be re-used with either a new (sterilized) lower plate member 35 and corresponding new needles 38, or a sterilzied re-used lower plate member 35 with its associated sterilized needles 38.

The needles 38 have a given length such that as the lower plate is moved downwardly toward the skin 40, the upper parts of the needles 38 leave the capsules 18 before the lower parts of the needles 38 prick the patient's skin. Thus, the allergens in the capsules 18 do not become contaminated since the needles are free of the capsules 18 when the skin is pricked, and the capsules 18 and the upper part of the assembly can be re-used without sterilization.

The capsules 18 are preferably removably mounted in the intermediate plate 14, for example via screw threads 41 at the intermediate portions of the capsule 18 as illustrated in the FIGS. 1–3. Alternatively, the capsules 18 may be press fit in a tight sliding manner into the apertures in the intermediate plate 14, or may be held in place by means of an adhesive. Preferably, such an adhesive is the type which can be easily broken to permit removal of the capsules 18 from plate 14, and replacement, as desired. As another alternative, respective set screws 42 can be provided on intermediate plate member 14 for each of the capsules 18, as shown in FIG. 5. After insertion of a capsule 18 into an aperture 17, the set screw 42 is tightened against the side of the capsule 18 to hold it in place. A similar set screw arrangement can be used to fix the intermediate plate 14 to the posts 10, 11.

Preferably, the upper closure member 19 of the capsules 18 is resilient rubber or other suitable resilient material so that when the projecting members 28 are received therein and pressure is downwardly applied, the upper closure 19 will yield downwardly and will create pressure inside the capsule 18 to enhance transfer of the allergen out of the capsule, through the hollow needle 38 pierced therein (see FIG. 2) and onto the skin of the user when the device is in the condition shown in FIG. 3.

A plurality of units 1 can be stacked side-by-side, as shown in FIG. 6. In FIG. 6, the outer units 1 are substantially identical to the units 1 of FIGS. 1-4. The middle unit 1' in FIG. 6 is also substantially identical to unit 1 of the embodiment of FIGS. 1-4, except that posts 10, 11 are not required in the middle unit. However, the middle unit 1 could be provided with posts 10, 11, as in the outer units 1. In the embodiment of FIG. 6, each unit 1, 1' comprises ten capsules 18, so that each unit enables ten allergy prick tests to be applied at the same time. The capsules of each unit may contain different allergens, thus enabling a prick test for up to thirty different substances to be applied at the same time, greatly enhancing efficiency, while each unit 1, 1' of the apparatus is described as having ten capsules each containing different allergens, a different number of capsules can be provided in each unit, as desired. The number of units which are connected together side-by-side, may be other than three. For example, the number of units connected together side-by-side is a function of the body area of the patient on which the test is to be performed. For example, if the test is to be performed on the arm of a patient, perhaps only one or two units 1 arranged side-by-side can be used. However, when the test is to be performed on the back of the patient, which is a relatively flat surface, three units or more 1, 1' connected together side-by-side can be advantageously used in some cases.

In FIG. 6, each side of the combined apparatus comprises a single upper handle 29' and a single lower handle 39' which extend between the outermost units 1. The side-by-side units are interconnected by means of male and female sockets and projections which cooperate to form respective interconnections 301. For example, the outer units 1 can comprise recesses 302 in the side walls thereof, and the intermediate unit 1' can comprise projections 303 extending from the side walls thereof for mating with the recesses 302. By providing such an arrangement, the center unit can be a special center unit, and the two outer units can be identical. Alternatively, the projections 303 can be provided on the side walls of the outer units 1, and the intermediate unit 1' can have recesses 302 for receiving the projections 303. Similar interconnections 301 are provided for the intermediate and/or lower plate members of the apparatus, in substantially the same manner as shown for the upper plate member. Alternatively, the units 1, 1' can be adhered together in the side-by-side relation, for example, by means of an adhesive or a solvent (if the plates are made of a suitable plastic material), or they may be otherwise connected for example by screws.

FIG. 7 shows a top view of an embodiment similar to the embodiment of FIG. 6, but wherein each of the units 1 comprises respective posts 10, 11. In FIG. 7, the interconnections 301 are shown as respective male-female (projection-recess) interconnections wherein the projections project from the upper and intermediate units, and the recesses are in the lower and intermediate units 1, as seen in FIG. 7.

The interconnections 301 in FIGS. 6 and 7 may be of the press-fit or interference-fit type to improve the integrity the interconnection. Snap-type connections may also be provided, such as shown in enlarged scale in FIG. 8. In FIG. 8, the projections 303 have a projecting rib 304, and the recesses 302 have a groove 305 therein to snappingly receive the ribs 304. This construction is particularly advantageous when the plate members (including the interconnections 301) are made of plastic material having some resiliency to permit the rib 304 to pass through the recess 302 and "snap" into a respective groove 305.

An advantage of the apparatus of the present invention is that the prick test is conducted at fixed predetermined spaced apart locations on the patient's skin. The spacing between the capsules 18 (and their associated needles 38) is arranged such that a sufficient distance is provided between adjacent needles so that the adjacent prick tests will not interfere with each other. In a preferred embodiment, the spacing "x" between adjacent needles (see FIG. 1) is approximately ½-¾ inch. A similar needle spacing is provided between adjacent needles of side-by-side connected units in the direction perpendicular to the direction "x" in FIG. 1. This eliminates the problem that respective prick tests may be applied too close to each other.

Preferably, the plate members 14, 25, 35 and the posts 10, 11 are fabricated of sterilizable plastic material, such as polyvinylchloride (PVC).

The capsules 18 are preferably made of glass or plastic material, and the needles, of course, are preferably made of metal, such as stainless steel.

An important advantage of the present invention is that the pricking or piercing of the skin is always done to a given skin penetration depth. The penetration depth is a function of the distance the needles 38 project downwardly from the lower plate member 35. See FIG. 3. Moreover, the skin penetration depth is replicable without requiring highly skilled operators, since the penetration depth is not a function of the skill of the operator, but is a function of the distance the needles 38 project downwardly from the lower plate member 35. Thus, repeatable results are obtainable when using the system of the present invention.

The upper plate-like member 25 is not absolutely required. The handles 29 can be coupled to the ends of the intermediate plate-like member 14. Handling and operation of the apparatus will be essentially similar to that described hereinabove. Also, the support rods or posts 10,11 need not be round. They may be rectangular, oval or any other convenient shape.

The term "allegen" is used throughout this specification and claims to denote the substance applied to a patient. However, the invention is equally applicable to antigens in general and the term "allergen" as used in the specification and claims denotes antigens as well as allergens.

It should be clear that various modifications and alterations can be made within the scope of the appended claims.

I claim:

1. An allergy testing apparatus for testing a patient for a plurality of allergies at substantially the same time, comprising:

a plurality of pricking means for pricking or piercing the skin of a patient;

carrier means including means for holding and supporting said plurality of pricking means with a given spacing between each of said pricking means, said holding and supporting means of said carrier means holding said plurality of pricking means normally in an inactive position out of contact with the skin of the patient, such that said plurality of pricking means are movable from said inactive position out of contact with the skin of a patient to an active position for pricking or piercing the skin of a patient;

means for applying respective allergens to at least some of said pricking means, while said pricking means are mounted in said holding and supporting means of said carrier means, so that said pricking means each applies its respective allergen to the skin when said pricking means are moved from said inactive position to said active position;

said carrier means further including skin engaging means for contacting the skin of a patient; and actuating means on said carrier means for substantially simultaneously moving all of said plurality of pricking means from said inactive position to said active position thereof, while said skin engaging means is in contact with the skin of a patient, to prick or pierce the skin of a patient and to thereby substantially simultaneously apply said respective allergens of all of said respective pricking means to the skin of the patient via said pricking means.

2. The allergy testing apparatus of claim 1, wherein said pricking means comprises a plurality of needles.

3. The allergy testing apparatus of claim 2, wherein said needles extend from said carrier means by a predetermined distance, so that said needles prick or pierce the skin of the patient to a predetermined controlled depth of penetration in said active position.

4. The allergy testing apparatus of claim 2, wherein said needles are hollow and said allergens pass through respective needles by capillary action.

5. The allergy testing apparatus of claim 1, wherein said pricking means, in said active position thereof, are out of communication with said allergen applying means.

6. The allergy testing apparatus of claim 1, wherein said holding and supporting means of said carrier means is movably coupled to said skin engaging means so as to be movable relative to said skin engaging means.

7. The allergy testing apparatus of claim 6, wherein said pricking means, in said active position thereof, are out of communication with said allergen applying means.

8. The allergy testing apparatus of claim 1, wherein said actuating means includes means for controlling movement of said pricking means to prick or pierce the skin of the patient in said active position to a predetermined controlled depth of penetration.

9. The allergy testing apparatus of claim 1, wherein said actuating means moves said holding and supporting means to thereby move said plurality of pricking means.

10. A method of testing a patient for a plurality of allergies at substantially the same time, comprising:
  holding and supporting a plurality of pricking means on a holding and supporting means with a given spacing between each of said pricking means, said plurality of pricking means being held and supported such that said plurality of pricking means are movable from an inactive position out of contact with the skin of a patient to an active position for pricking or piercing the skin of a patient, said pricking means being normally held and supported in said inactive position;
  applying respective allergens to at least some of said pricking means, while said pricking means are mounted on said holding and supporting means, so that said pricking means each applies its respective allergen to the skin when said pricking means are moved from said inactive position to said active position;
  mounting a skin engaging member of said holding and supporting means on the skin of a patient such that said pricking means in said normally inactive position are out of contact with the skin of the patient; and
  substantially simultaneously moving all of said plurality of pricking means from said inactive position to said active position thereof, while said skin engaging means is in contact with the skin of a patient, to prick or pierce the skin of a patient and to thereby substantially simultaneously apply said respective allergens of all of said respective pricking means to the skin of the patient via said pricking means.

11. The method of claim 10, wherein said pricking means comprises a plurality of needles, and wherein said applying step comprises applying said respective allergens to respective needles.

12. The method of claim 11, wherein said needles extend from said holding and supporting means by a predetermined distance wherein said moving step includes controlling movement of said needles to prick or pierce the skin of the patient in said active position to a predetermined controlled depth of penetration.

13. The method of claim 11, wherein said needles are hollow and said allergens pass through respective needles by capillary action.

14. The method of claim 10, comprising keeping said pricking means, in said active position thereof, out of communication with said allergen applying means.

15. The method of claim 10, wherein said moving step comprises moving said holding and supporting means relative to said skin engaging means.

16. The method of claim 15, comprising keeping said pricking means, in said active position thereof, out of communication with said allergen applying means.

17. The method of claim 10, wherein said moving step includes controlling movement of said pricking means to prick or pierce the skin of the patient in said active position to a predetermined controlled depth of penetration.

18. The method of claim 10, wherein said moving step comprises moving said holding and supporting means to thereby move said plurality of pricking means.

* * * * *